(12) United States Patent
Kim et al.

(10) Patent No.: US 7,374,577 B2
(45) Date of Patent: May 20, 2008

(54) IMPLANT DEVICE FOR OSSEOINTEGRATION TO ENDURE WEIGHT

(75) Inventors: Shin Ki Kim, Seoul (KR); Moo Sung Moon, Seoul (KR); Jae Yong Ahn, Seoul (KR)

(73) Assignee: Workers Accident Medical Corporation, Seoul (KR)

( * ) Notice: Subject to any disclaimer, the term of this patent is extended or adjusted under 35 U.S.C. 154(b) by 215 days.

(21) Appl. No.: 11/317,419

(22) Filed: Dec. 22, 2005

(65) Prior Publication Data
US 2007/0150070 A1 Jun. 28, 2007

(51) Int. Cl.
*A61F 2/60* (2006.01)
(52) U.S. Cl. .................... 623/32; 623/16.11
(58) Field of Classification Search ............. 623/32, 623/23.46, 16.11
See application file for complete search history.

(56) References Cited

U.S. PATENT DOCUMENTS

2004/0068324 A1* 4/2004 Grundei .............. 623/32

* cited by examiner

*Primary Examiner*—Bruce Snow
(74) *Attorney, Agent, or Firm*—Sheridan Ross P.C.

(57) ABSTRACT

Disclosed herein is an implant device for osseointegration to endure weight. This implant device includes an insert-type implant inserted into an amputated end of a thighbone or a lower leg bone of a leg of a patient; a load dispersing adaptor having a cap shape, encompassing both the implant and the amputated end of the leg simultaneously at a lower end of the implant; a load support plate having a plate shape, coupled with the lower surface of the adaptor, whose diameter is widened, on which a plurality of muscle fixing holes are dispersedly formed; and a coupling screw, which couples the load dispersing adaptor with the insert-type implant at a bottom of the load dispersing plate through screw-coupling.

2 Claims, 5 Drawing Sheets

IMPLANT DEVICE FOR OSSEOINTEGRATION TO ENDURE WEIGHT

BACKGROUND OF THE INVENTION

1. Field of the Invention

The present invention relates generally to implant devices for osseointegration to endure weight and, more particularly, to an implant device for osseointegration to endure weight, whereby osseointegration is possible by mounting an implant vertically into an amputated end of a thighbone or a lower leg bone, both of which constitute the leg of a patient, and by coupling both a load dispersing adapter and a load support plate to the implant, thus dispersing load to the socket of a prosthetic leg and allowing the patient to conveniently use the prosthetic leg.

2. Description of the Related Art

Generally, a prosthesis is an artificial replacement to compensate for physical shortage of the legs of a patient, which is in close contact with the stump of a lost body part (among the legs), has a plurality of functions, has an external appearance closely resembling human's legs, and can be attached and used in a stable manner.

According to a body part which is physically lost, for which attachment of the prosthesis is needed, there are upper leg amputation when the upper leg is amputated, lower leg amputation when the lower leg is amputated, and disarticulation when any of articulations of the upper leg or the lower leg is amputated.

As illustrated in FIG. 1, the lower leg amputation includes toe amputation A to amputate a toe; tarsometatarsal amputation B to horizontally amputate a tarsometatarsal bone, in which a surgical operation to do this is referred to as "Lisfranc's disarticulation"; Chopar's amputation C to disarticulate the ankle bone inferior navicular and the lateral talus cuboid bone joints to thereby remain only the ankle bone and the lateral talus; Syme amputation D to amputate between the distal portion of the tarsometatarsal bone and that of 1/3 of a lower leg bone; below-knee (B-K) amputation E to amputate the lower leg bone 1 below the knee joint more proximal than the Syme amputation; knee disarticulation F to amputate the lower leg bone below the knee joint; above-knee (A-K) amputation G to amputate a thighbone 2 over the knee joint; hip disarticulation H that is surgically operated to completely remove the thighbone below the hip joint, thus treating malignant tumor, such as osteogenic sarcoma or cartilaginous sarcoma in the proximal portion of the thighbone; hemipelvectomy I to amputate one side of the pelvis and the entire lower leg; and hemicorporectomy J to amputate the lower half of one's body below the 3-4 numbered lumbar.

Especially, as illustrated in FIG. 2, the prosthetic leg due to amputation of the thighbone basically comprises a foot-ankle assembly 10, a shank 11, a knee assembly 12, a socket 13 and a suspension device (not shown).

The shank 20 of the thighbone prosthetic leg connects the foot assembly 10 to the knee assembly 12. The shank 20 may be made by cutting wood to be shaped as the lower leg of a person and covering it with plastic, or a metallic or PVC pipe may be used as an endoskeleton and the surface thereof is covered with a smooth and agreeable material for external beauty, which resembles the human's leg.

The knee assembly 12 is mainly used as a single axis.

Of course, the lower prosthetic leg used to compensate for amputation of the lower leg bone comprises a socket and an artificial foot.

The socket 13 employs entire contact, partial weight application and combination thereof, according to a load application type to an amputated portion. Depending upon the extent of using the remaining muscle of the amputated portion, the load applied to the socket varies, which brings the diversity in one's manner of walking. If a load is concentrically applied to both the amputated portion and the socket or the load is dispersedly applied to the entire part of the amputated portion, a scratch or dermatitis may be generated due to friction between the skin of the patient at the contact region and the socket. Accordingly, a patient who is wearing the lower prosthetic leg for a long period cannot correctly walk because of pains.

SUMMARY OF THE INVENTION

Accordingly, the present invention has been made keeping in mind the above problem in the prior art, and an object of the present invention is to provide an implant device for osseointegration to endure weight, in which an implant is inserted into the thighbone or the lower leg bone of a patient having an amputated leg and couples a weight support plate to the bone, thereby increasing the contact surface area of the implant device relative to a socket and allows the patient to conveniently use a prosthetic leg.

In order to accomplish this and other objects, a hole is formed along a central axis in the lower end of the thighbone or the lower leg bone of an amputated leg, through which an implant is inserted, a load dispersing adaptor is placed around the lower end of the implant, the adaptor having a space to encompass both the bone and the lower end of the implant simultaneously, a load support plate is placed at the lower end of the load dispersing adaptor, the plate having an increasing lower surface, and, thereafter, both the load supporting plate and the load dispersing adaptor are mounted to the implant using a screw.

According to an aspect of the present invention, there is provided an implant device for osseointegration to endure weight, comprising: an insert-type implant inserted into an amputated end of the thighbone or the lower leg bone of a leg of a patient; a load dispersing adaptor having a cap shape, encompassing both the implant and the amputated end of the leg simultaneously at a lower end of the implant; a load support plate having a plate shape, coupled with a lower surface of the adaptor, whose diameter is widened, on which a plurality of muscle fixing holes are dispersedly formed; and a coupling screw, which couples the load dispersing adaptor with the insert-type implant at a bottom of the load dispersing plate through screw-coupling.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENT

Figure 1:
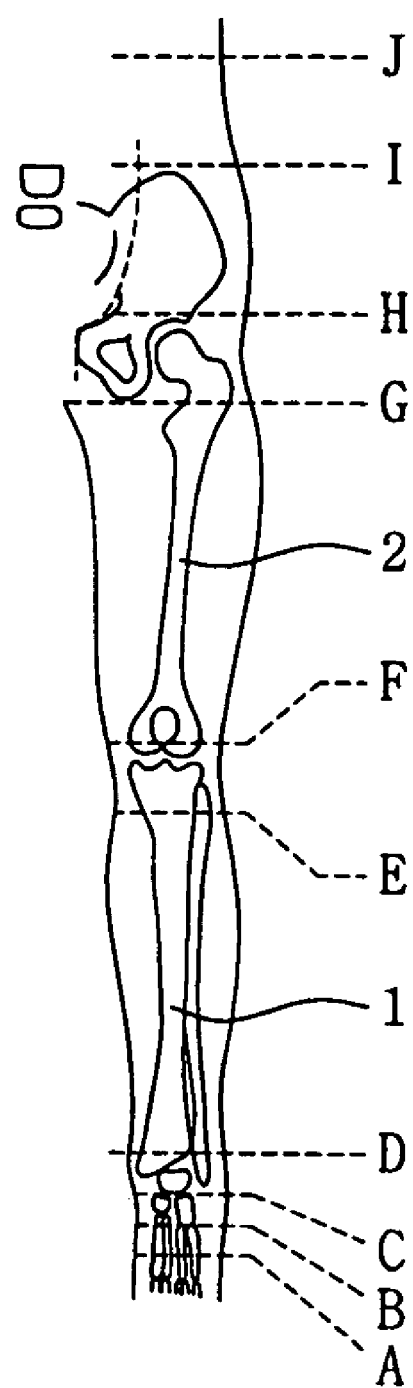
FIG. 1 shows a leg having common leg amputation.
Figure 2:
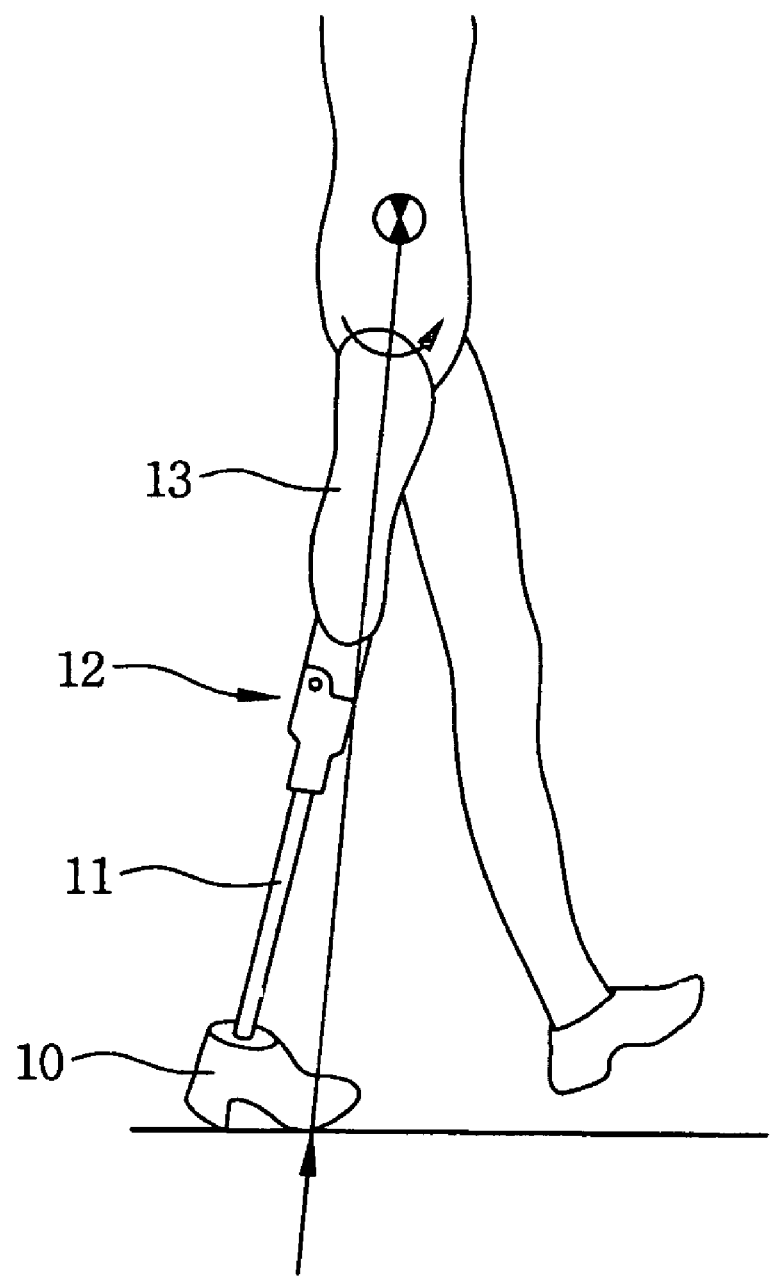
FIG. 2 shows an example of a prosthetic leg according to the amputated thigh.

Reference now should be made to the drawings, in which the same reference numerals are used throughout the different drawings to designate the same or similar components.

Herein below, a preferred embodiment of the present invention will be described in more detail with reference to the accompanying drawings.

Figure 3:
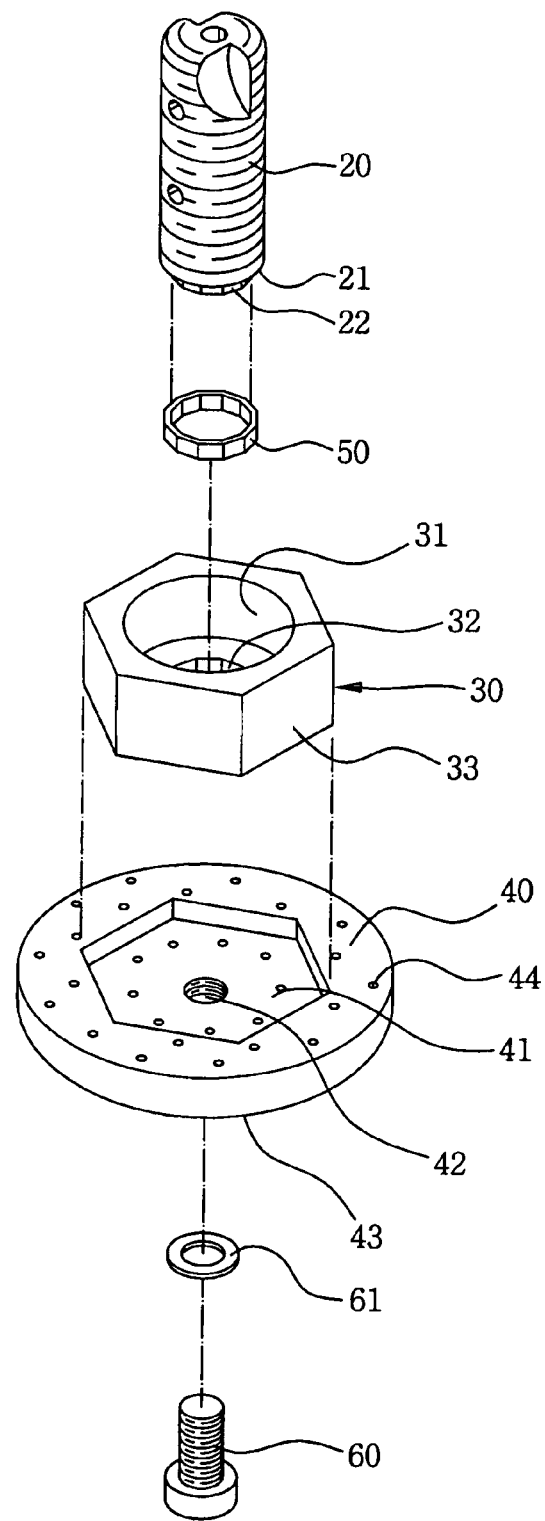
FIG. 3 is an exploded perspective view of an implant device according to an embodiment of the present invention.
Figure 4:
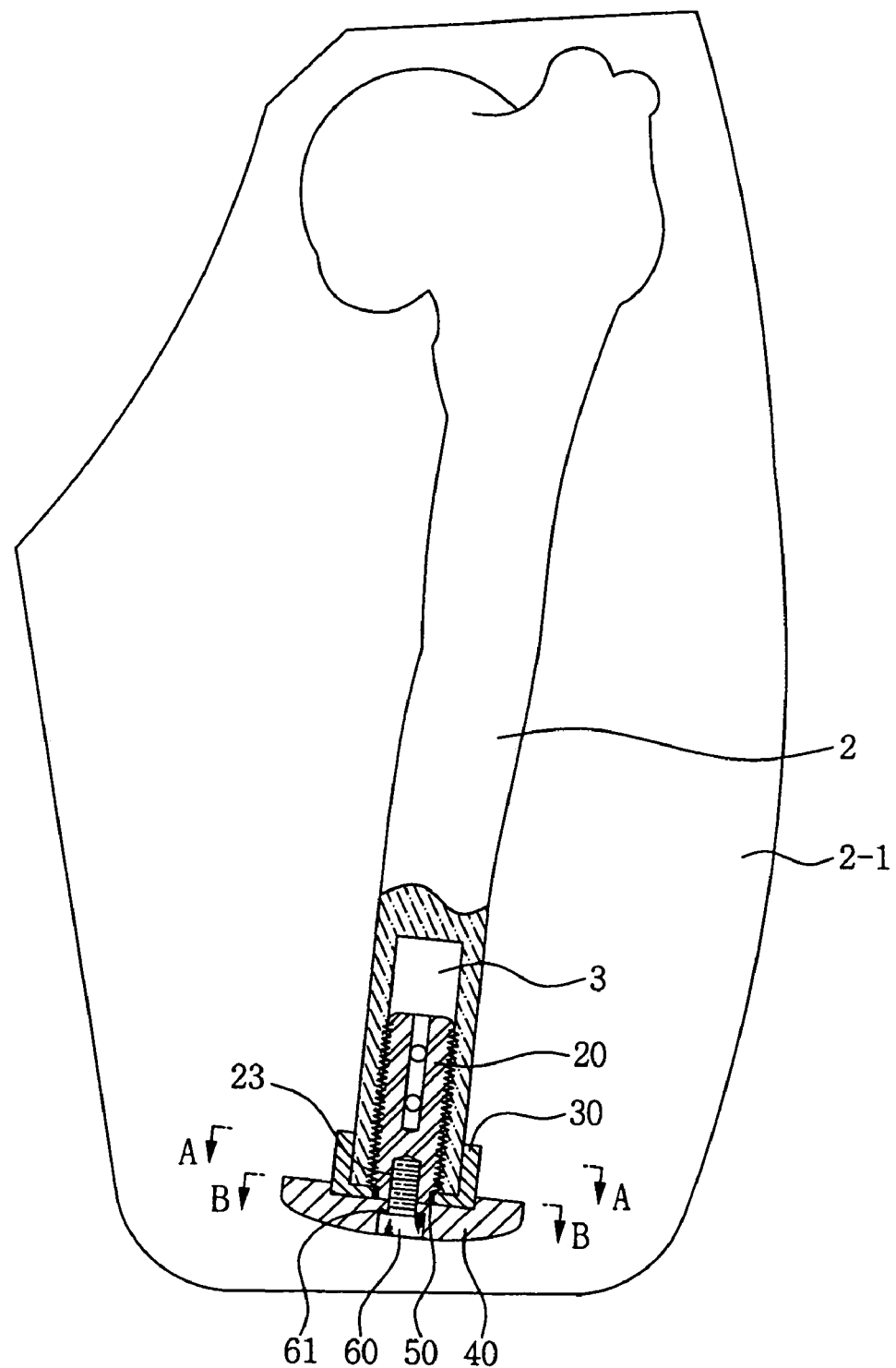
FIG. 4 is a partially sectioned view showing a state that the implant device according to the present invention is inserted into the thighbone of a patient.
Figure 5:
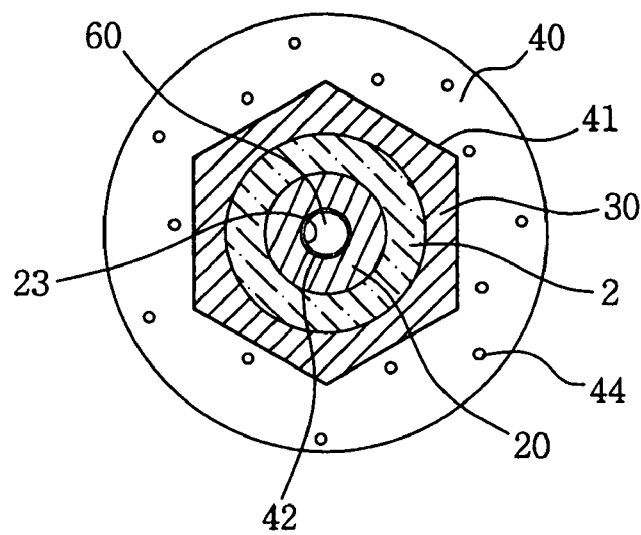
FIG. 5 is a sectional view taken along line A-A of FIG. 4.
Figure 6:
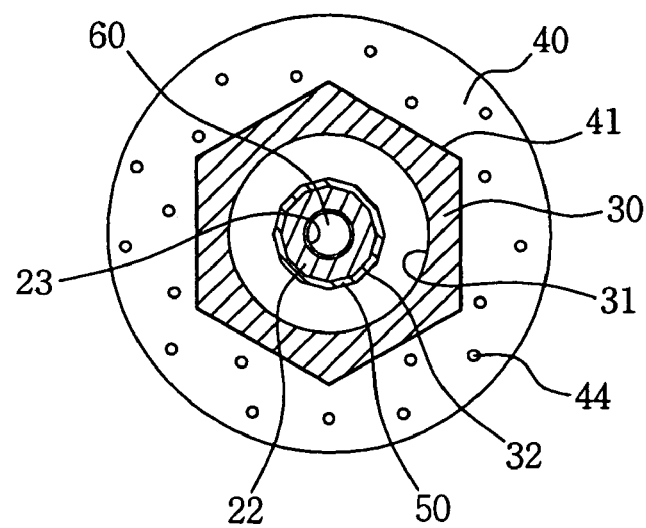
FIG. 6 is a sectional view taken along line B-B of FIG. 4.

FIG. 3 is an exploded perspective view of an implant device according to an embodiment of the present invention. FIG. 4 is a partially sectioned view showing a state that the implant device according to the present invention is inserted into the thighbone of a patient. FIG. 5 is a sectional view taken along line A-A of FIG. 4. FIG. 6 is a sectional view taken along line B-B of FIG. 4. As illustrated in the drawings, the implant device of this invention comprises an insert-type implant 20, which is tightened into an insert hole 3 that is formed vertically in a thighbone 2 or a lower leg bone 1 of a patient, both of which constitute a leg. This implant 20 has a polygonal rib 22 on the lower end thereof, with a step having a reduced diameter formed on the rib 22. A load dispersing adaptor 30 having an adaptor hole 31 encompasses both the outer circumferential surface of the implant 20 and the lower part of the outer circumferential surface of the amputated thighbone 2. A polygonal hole 32 is formed in the lower end of the adapter 30, into which a polygonal rotation preventing ring 50 is engaged. A load support plate 40 has an adaptor coupling hole 41 in the upper surface thereof, through which the load dispersing adaptor 30 is coupled. The adaptor coupling hole 41 has a screw hole 42 and a plurality of muscle fixing holes 44 formed dispersedly in order to fix the muscle. A polygonal rotation preventing ring 50 is seated between the polygonal rib 22 and the polygonal hole 32, thereby preventing the adapter 30 from being rotated relative to the implant 20. A coupling screw 60 is fastened to the lower end of the implant 20, thus mounting both the load support plate 40 and the load dispersing adaptor 30 to the implant 20. The interface between the insert-type implant 20 and the polygonal rib 22 is formed with a step 21 having a reduced diameter. The reference numeral 3 denotes the muscle and the skin of the leg.

The lower surface of the load support plate 40 desirably has a curved surface 43 to disperse the weight of the patient having the amputated leg.

The outer circumferential surface of the load dispersing adaptor 30 forms a hexagonal nut surface 33, and the upper surface of the load support plate 40 has an adaptor coupling hole 41 whose wall surface is cubed to accommodate the hexagonal nut surface 33.

To use the implant device according to the present invention configured as described above on a patient whose leg is amputated, e.g., a thighbone amputated patient, the muscle around the amputated thighbone 2 is amputated to expose the end of the thighbone 2. Thereafter, an insert hole 3 is formed vertically in the lower end of the thighbone 2 and the implant 20 is inserted into the insert hole 3, as illustrated in FIG. 3. In this case, the implant 20 is coupled in such a manner as to allow the polygonal rib 22 thereof to be exposed outside the lower end of the thighbone 2.

Subsequently, the load dispersing adaptor 30 is seated in the adaptor coupling hole 41 of the load dispersing plate 40 on the lower end of the thighbone 2 in such a manner as to encompass the lower end of the thighbone 2 and the insert-type implant 20. The outer circumferential surface of the adaptor 30 is formed with the cubed nut surface 33, like a general nut, and thus, it can be jointly coupled with a screw through screw-coupling using a conventional tool, which must be subjected to disinfection.

The polygonal rotational preventing ring 50 is seated in the space between the polygonal hole 32 communicating with the center of the adaptor hole 31, formed in the lower surface of the load dispersing adaptor 30, and the polygonal rib 22 so that the load dispersing adaptor 30 is closely fastened to the insert-type implant 20.

The load support plate 40 is inserted into the adaptor coupling hole 41, which has the wall surfaces corresponding to the nut surfaces 33, so that a rotation of the adaptor coupling hole 41 can be prevented. When the coupling screw 60 is tightened into the screw hole 42 of the implant 20, the externally threaded part of the coupling screw 60 engages with the inner-threaded screw hole 23. Using a part of the plurality of muscle fixing holes 44 formed dispersedly on the load support plate 40, the amputated muscles are firmly stitched with a surgery thread, and the muscles are mutually sealed.

Thereafter, the muscle part, which forms the end of the sealed thighbone 2, should be strengthened through exercise, so as to endure the weight.

To a patient who uses the implant device of the present invention, by coupling the implant into an inner end of the socket for a prosthetic leg through amputation, the load is dispersed to the corresponding muscle part. Accordingly, the gravity resistance of the unit muscle is increased so that fewer pains on the muscle are applied although a direct load is applied to the socket, thereby enabling the patient to conveniently this device for a long time. An embodiment of the present invention has been described, based on the amputation of the thighbone 2, but which is an example. The same construction can be used for an amputated lower leg bone, but illustration and description thereof will be omitted.

As described above, according to the present invention, when a thighbone or a lower leg bone constituting the leg part of a patient is amputated, an implant is vertically tightened into the lower end of the amputated bone. The implant is, thereafter, coupled to a load dispersing adaptor, which encompasses the outer circumferential surface of the amputated leg. A load support plate, whose lower diameter is increased, is coupled to the lower end of the implant using a screw with the load dispersing adaptor. Thus, the contact surface area of the load support plate relative to the muscle surrounding the load support plate is increased. Accordingly, in the case of a patient using the implant device according to the present invention in his/her amputated leg, the amount of applied load per unit area of the muscle in the corresponding portion is reduced. Thus, the patient can endure a direct load using the socket, which couples the prosthetic leg to the body of the patent.

By enduring the direct load using the socket, even the patient whose leg is amputated can increase the time of wearing the prosthetic leg, but pains resulting from this wearing can be reduced.

As a result, since the skin (muscle) thickness on the end of the amputated portion is maintained as minimum as possible, the load state generated in walking is directly transferred to the bone, and the patient can walk with detecting the walking state utilizing the sensing ability of the bone as maximum as possible.

In addition, according to the present invention, the implant and the load dispersing adaptor are mutually prevented from rotation owing to the polygonal rotation preventing ring, thereby maintaining their states constantly to thereby increasing the durability. Since both the load dispersing adaptor and the load support plate are also coupled on the right position using the coupling hole structure corresponding to the nut surface, the load support plate is also coupled on a constant position by preventing the rotation on the right position, thereby minimizing the side effects resulting from wearing this device.

The lower surface of the load support plate is curved, to thereby increase the contact area with the muscle portion encompassing it after operation, and as well can be used even by the whole contact with the socket, forming a curved surface similar to the inner surface of the socket. Accordingly, even a patient having an amputated leg can conveniently use the device.

Further, since a plurality of muscle fixing holes is randomly formed on the load support plate, the muscle can be firmly coupled with the muscle fixing holes with the surgery thread. As the muscle grows, this will prevent movement of the muscle on the end of the amputated part, thereby increasing the durability in use.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. An implant device for osseointegration to endure weight, comprising:

an insert-type implant is capable of being inserted into an amputated end of a thighbone or a lower leg bone of a leg of a patient;

a load dispersing adaptor having a cap shape, sized to encompass both the implant and the amputated end of the leg simultaneously at a lower end of the implant, and having an outer circumferential surface formed as a hexagonal nut surface;

a load support plate having a plate shape, coupled with a lower surface of the adaptor, whose diameter is widened, on which a plurality of muscle fixing holes are dispersedly formed and the upper surface thereof provided with a polygonal adaptor seat depression, which has diametrically opposite wall surfaces corresponding to the shape of the hexagonal nut surface to accommodate the hexagonal nut surface; and a coupling screw, which couples the load dispersing adaptor with the insert-type implant at a bottom of the load dispersing plate through screw-coupling.

2. The implant device as claimed in claim 1, wherein a polygonal rib is formed on a lower surface of the implant, with a step having a reduced diameter formed on the lower end of the implant, a polygonal hole formed on a lower surface of the load dispersing adaptor, and a polygonal rotation preventing ring to prevent rotation interposed between the polygonal rib and the polygonal hole.

* * * * *